United States Patent
Rateick

(10) Patent No.: US 9,678,029 B2
(45) Date of Patent: Jun. 13, 2017

(54) OXIDATION CATALYST DETECTOR FOR AIRCRAFT COMPONENTS

(71) Applicant: Honeywell International Inc., Morristown, NJ (US)

(72) Inventor: Richard Rateick, South Bend, IN (US)

(73) Assignee: Honeywell International Inc., Morris Plains, NJ (US)

( * ) Notice: Subject to any disclaimer, the term of this patent is extended or adjusted under 35 U.S.C. 154(b) by 75 days.

(21) Appl. No.: 14/466,714

(22) Filed: Aug. 22, 2014

(65) Prior Publication Data

US 2016/0054249 A1  Feb. 25, 2016

(51) Int. Cl.
*G01N 27/12* (2006.01)
*F16D 66/00* (2006.01)
(Continued)

(52) U.S. Cl.
CPC .............. *G01N 27/12* (2013.01); *B60T 17/18* (2013.01); *B60T 17/22* (2013.01); *B64D 45/00* (2013.01);
(Continued)

(58) Field of Classification Search
CPC ........ G01N 27/12; G01N 27/06; G01N 27/20; B60T 17/18; B60T 17/22; B64D 45/00; F16D 66/00
(Continued)

(56) References Cited

U.S. PATENT DOCUMENTS 3,873,927 A   3/1975 Overall
4,135,151 A   1/1979 Rogers et al.
(Continued)

FOREIGN PATENT DOCUMENTS

CN   1704754 A   12/2005
CN   102901750 A   1/2013
(Continued)

OTHER PUBLICATIONS

Hille et al., "Deicing and Anti-icing Fluid Residues," AeroMagazine, retrieved from http://www.boeing.com/commercial/aeromagazine/articles/qtr_1_07/AERO_Q107_article3.pdf, Aero Quarterly, Jan. 2007, 8 pp.
(Continued)

*Primary Examiner* — Patrick Assouad
*Assistant Examiner* — Kristopher Yodichkas
(74) *Attorney, Agent, or Firm* — Shumaker & Sieffert, P.A.

(57) ABSTRACT

The exposure of an aircraft component to an oxidation catalyst, such as a deicing solution, may be detected with the aid of an electrical conductivity sensor. In some examples, a system includes an aircraft component, an electrical conductivity sensor mechanically connected to the aircraft component and configured to generate an output, and a processor configured to detect an oxidation catalyst exposure event based on the output generated by the electrical conductivity sensor. The electrical conductivity sensor may be configured and positioned to generate a signal indicative of electrical conductivity of a substance to which the aircraft component is exposed. The processor may be configured to detect an oxidation catalyst exposure event by at least determining whether the electrical conductivity indicated by the signal is greater than or equal to a predetermined conductivity threshold value.

18 Claims, 5 Drawing Sheets

(51) Int. Cl.
*B60T 17/22* (2006.01)
*G01N 27/06* (2006.01)
*B64D 45/00* (2006.01)
*B60T 17/18* (2006.01)
*G01N 27/20* (2006.01)

(52) U.S. Cl.
CPC ............ *F16D 66/00* (2013.01); *G01N 27/06* (2013.01); *G01N 27/20* (2013.01)

(58) Field of Classification Search
USPC .......................................................... 324/693
See application file for complete search history.

(56) References Cited

U.S. PATENT DOCUMENTS

| | | | |
|---|---|---|---|
| 4,227,151 A | 10/1980 | Ellis et al. | |
| 4,745,803 A | 5/1988 | Haavasoja | |
| 5,206,806 A | 4/1993 | Gerardi et al. | |
| 5,331,287 A * | 7/1994 | Yamagishi | G01N 27/121 204/421 |
| 5,497,100 A | 3/1996 | Reiser et al. | |
| 5,523,959 A * | 6/1996 | Seegmiller | B64D 15/20 244/134 F |
| 5,596,320 A | 1/1997 | Barnes | |
| 5,772,153 A | 6/1998 | Abaunza et al. | |
| 5,904,321 A | 5/1999 | Cox et al. | |
| 5,942,753 A | 8/1999 | Dell | |
| 6,052,056 A | 4/2000 | Burns et al. | |
| 6,194,999 B1 | 2/2001 | Uhl et al. | |
| 6,295,868 B1 | 10/2001 | Cooper | |
| 6,341,670 B1 | 1/2002 | Leblanc et al. | |
| 6,442,457 B1 | 8/2002 | Jones et al. | |
| 6,501,375 B1 | 12/2002 | Weant et al. | |
| 6,535,141 B1 * | 3/2003 | Doherty | A01C 17/00 340/580 |
| 6,696,937 B1 | 2/2004 | Kiefer | |
| 6,825,758 B1 | 11/2004 | Laitsaari | |
| 6,894,512 B2 * | 5/2005 | Girshovich | G01N 27/121 324/694 |
| 6,995,572 B2 | 2/2006 | Arndt et al. | |
| 7,118,805 B2 | 10/2006 | Walker et al. | |
| 7,129,846 B2 | 10/2006 | Rasmussen et al. | |
| 7,333,219 B2 | 2/2008 | Yu et al. | |
| 7,337,662 B2 | 3/2008 | Sato et al. | |
| 7,368,231 B2 | 5/2008 | Yuan | |
| 7,371,503 B2 | 5/2008 | Miyamatsu et al. | |
| 7,629,801 B2 | 12/2009 | Keep et al. | |
| 7,733,479 B2 | 6/2010 | Shew et al. | |
| 7,872,379 B2 | 1/2011 | Fuller et al. | |
| 7,877,216 B2 | 1/2011 | Wright et al. | |
| 8,009,027 B2 | 8/2011 | Thomas et al. | |
| 8,044,823 B2 | 10/2011 | Doherty et al. | |
| 8,151,944 B2 | 4/2012 | Waltz | |
| 8,186,208 B2 | 5/2012 | Matsumura | |
| 8,224,595 B2 | 7/2012 | Hefner et al. | |
| 8,292,230 B2 | 10/2012 | DeSmet | |
| 8,310,356 B2 | 11/2012 | Evans et al. | |
| 8,319,623 B2 | 11/2012 | Wallace et al. | |
| 8,350,571 B2 | 1/2013 | Son | |
| 8,375,781 B2 | 2/2013 | Paul et al. | |
| 8,409,425 B2 | 4/2013 | Forrow et al. | |
| 8,421,612 B2 | 4/2013 | Sugiura | |
| 8,599,044 B2 | 12/2013 | Maggiore et al. | |
| 8,717,159 B2 | 5/2014 | Todd et al. | |
| 2004/0189331 A1 | 9/2004 | Girshovich et al. | |
| 2006/0042734 A1 | 3/2006 | Turner et al. | |
| 2007/0026153 A1 * | 2/2007 | Nicolaus | C04B 35/632 427/372.2 |
| 2008/0194292 A1 | 8/2008 | Naito et al. | |
| 2009/0074613 A1 | 3/2009 | Kaindl et al. | |
| 2009/0224901 A1 | 9/2009 | Yu | |
| 2009/0229926 A1 | 9/2009 | Schaefer | |
| 2011/0040518 A1 | 2/2011 | Schmitz-Hubsch | |
| 2011/0222055 A1 | 9/2011 | Durickovic et al. | |
| 2011/0241866 A1 | 10/2011 | Todd et al. | |
| 2012/0139751 A1 | 6/2012 | Lin | |
| 2013/0157350 A1 | 6/2013 | Slocum et al. | |
| 2013/0240665 A1 * | 9/2013 | Cox | B64C 25/405 244/50 |
| 2014/0011455 A1 | 1/2014 | Hsu et al. | |
| 2014/0060012 A1 | 3/2014 | Kakimoto | |
| 2014/0143022 A1 | 5/2014 | Wisniewski | |
| 2015/0204776 A1 * | 7/2015 | Balmond | G01R 27/08 324/700 |

FOREIGN PATENT DOCUMENTS

| | | |
|---|---|---|
| CN | 103149206 A | 6/2013 |
| DE | 4029615 A1 | 4/1992 |
| EP | 0241676 A2 | 10/1987 |
| EP | 1275014 A2 | 1/2003 |
| FR | 2743632 A1 | 7/1997 |
| FR | 2792324 A1 | 10/2000 |
| JP | 3703062 B2 | 10/2005 |
| KR | 101192992 | 10/2012 |
| WO | 0187897 A1 | 11/2001 |
| WO | 0204290 A1 | 1/2002 |
| WO | 2009059978 A1 | 5/2009 |
| WO | 2013069014 A1 | 5/2013 |

OTHER PUBLICATIONS

Extended Search Report from counterpart European Application No. 15181304.5, dated Dec. 15, 2015, 9 pp.
U.S. Appl. No. 14/030,805, by Carl Esposito, filed Sep. 18, 2013.
"The Active Road and Runway Condition Sensor", Frensor, downloaded from http://www.asft.se/pdf/weather/Frensor_ASFT.pdf on Aug. 22, 2014 (2 pages).
Park et al., A Miniature Electrolytic Conductivity Probe with a Wide Linear Range. Electroanalysis, 19: Abstract (Sep. 2007).
Response to Extended Search Report dated Dec. 15, 2015, from counterpart European Application No. 15181304.5, filed Aug. 11, 2016, 11 pp.
Examination Report from counterpart European Application No. 15181304.5, dated Nov. 30, 2016, 5 pp.
Response to Examination Report dated Nov. 30, 2016, from counterpart European Application No. 15181304.5, filed Mar. 23, 2017, 22 pp.

* cited by examiner

OXIDATION CATALYST DETECTOR FOR AIRCRAFT COMPONENTS

TECHNICAL FIELD

This disclosure relates to aircraft braking systems.

BACKGROUND

A brake assembly of an aircraft has a limited useable life, as determined through wear, and may have an associated operating and maintenance cost that is based on the actual use of the brake assembly and how fast the life of the brake assembly is consumed. As a result of varying external factors and varying frictional forces during braking events, different aircraft brake assemblies may experience different rates of wear over time.

SUMMARY

Devices, systems, and techniques for detecting the exposure of an aircraft component to an oxidation catalyst, such as a deicing solution, are described herein. The aircraft component may be, for example, a component of an aircraft brake assembly, an aircraft wheel well or landing gear, an aircraft fuselage, or another aircraft structure. In some examples, an electrical conductivity sensor is configured and positioned to generate a signal indicative of electrical conductivity of a substance to which the aircraft component is exposed. A processor is configured to detect an oxidation catalyst exposure event by at least receiving the signal from the sensor and determining whether the electrical conductivity indicated by the signal is greater than or equal to a predetermined conductivity threshold value. In response to determining the electrical conductivity indicated by the signal is greater than or equal to a predetermined conductivity threshold value, the processor may generate an indication of an exposure event and, e.g., store the indication in a memory. In some examples, the exposure events detected in this manner may be used to determine the life of the aircraft component.

In one example, the disclosure is directed to a system comprising an aircraft component, an electrical conductivity sensor mechanically connected to the aircraft component and configured to generate an output, and a processor configured to detect an oxidation catalyst exposure event based on the output generated by the electrical conductivity sensor.

In another example, the disclosure is directed to a method comprising receiving, by a processor, an output of an electrical conductivity sensor mechanically connected to an aircraft component, detecting, by the processor, an oxidation catalyst exposure event based on the output, generating, by the processor, an indication of the oxidation exposure event, and storing the indication of the oxidation exposure event in a memory of a device.

In another example, the disclosure is directed to a system comprising means for sensing electrical conductivity of a substance to which an aircraft component is exposed, and means for detecting an oxidation catalyst exposure event based on an output of the means for sensing electrical conductivity.

The disclosure is also directed to an article of manufacture comprising a computer-readable storage medium. The computer-readable storage medium comprises computer-readable instructions that are executable by a processor. The instructions cause the processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory or storage element that stores instructions (e.g., in the form of a computer program or other executable) to cause a processor to perform the techniques described herein. The computer-readable medium may be a non-transitory storage medium.

The details of one or more examples are set forth in the accompanying drawings and the description below. Other features, objects, and advantages of the disclosure will be apparent from the description and drawings, and from the claims.

DETAILED DESCRIPTION

Figure 1:
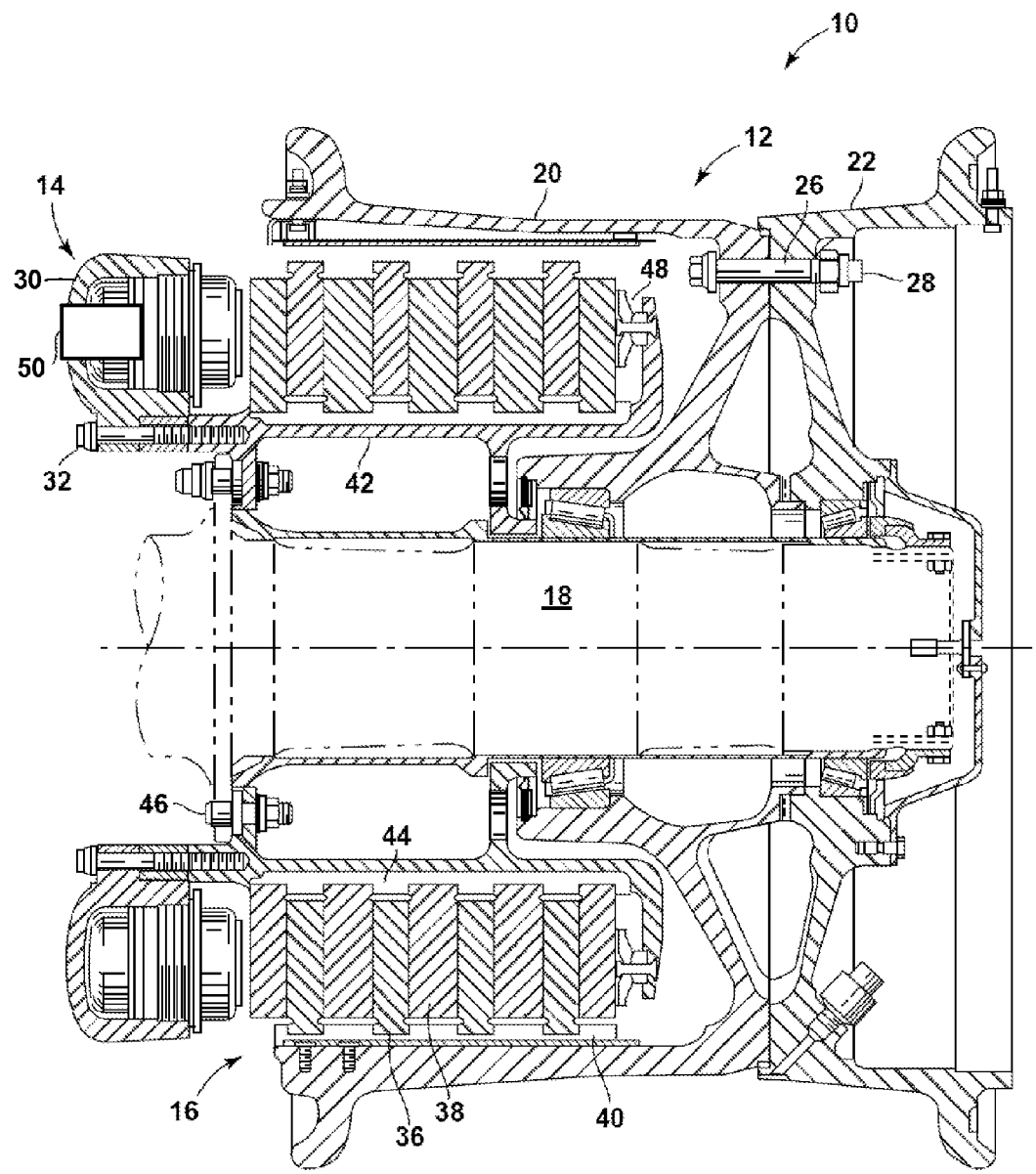
FIG. 1 is a schematic diagram illustrating an example aircraft brake assembly and an electrical conductivity sensor mechanically connected the aircraft brake assembly.

One or more components of an aircraft (e.g., carbon-carbon brake discs or other components of an aircraft brake assembly, or other aircraft structural elements) may be exposed to runway deicing fluids, e.g., during a ground operation of the aircraft. Some deicing fluids may increase in an oxidation rate of some aircraft components (e.g., carbon-carbon brake discs or other components of an aircraft brake assembly, or other aircraft structural elements), which may shorten the useful life of the aircraft component. For example, runway deicing fluids including alkali metal and alkaline earth carboxylates may catalyze oxidation of carbon. At least some runway deicing fluids that act as an oxidation catalyst may be electrically conductive. For example, runway deicing fluids that may catalyze carbon aircraft components (components formed from carbon) are relatively highly ionic in aqueous solutions (e.g., relative to tap water and distilled water). As an example, some runway deicing fluids currently being used comprise alkali metal and alkaline earth based carboxylates that exhibit an electrical conductivity of 30 millisiemens per centimeter (mS/cm) or more, such as 50 mS/cm to about 100 mS/cm. Accordingly, exposure of an aircraft component to an electrically conductive deicing fluid or other electrically conductive oxidation catalysts may be detected based on the electrical conductivity of a substance to which the aircraft component is exposed.

Example devices, systems, and techniques for detecting the exposure of an aircraft component to an electrically conductive oxidation catalyst, such as a deicing fluid, are described herein. The exposure of an aircraft component to an electrically conductive oxidation catalyst may be referred to as an "oxidation catalyst exposure event." The aircraft component can be, for example, an aircraft brake assembly (or a specific element thereof), an aircraft wheel well or landing gear, an aircraft fuselage, or another aircraft structure. Detection of the exposure of one or more aircraft components to the deicing fluid may be useful for various purposes, such as predicting the useful life of the aircraft component. For example, aircraft operating in airfields where climates require runway deicing may experience shortened brake life as opposed to aircrafts operating in areas without runway deicing.

In some examples, an oxidation catalyst exposure event may be detected with the aid of an electrical conductivity sensor, which positioned relative to the aircraft component to detect the electrical conductivity of substances to which the component is exposed. For example, a system may include an electrical conductivity sensor mechanically connected to an aircraft component and configured to generate a signal indicative of electrical conductivity of a substance to which the aircraft component is exposed. A processor of the system is configured to receive the signal from the sensor and determine whether the electrical conductivity indicated by the signal is greater than or equal to a predetermined conductivity threshold value. If the electrical conductivity indicated by the signal is greater than or equal to the predetermined conductivity threshold value, then the processor may determine that the substance to which the sensor was exposed is an electrically conductive oxidation catalyst. Thus, in some examples, in response to determining the electrical conductivity indicated by the signal is greater than or equal to the predetermined conductivity threshold value, the processor may generate an indication of an oxidation catalyst exposure event and, for example, store the indication in a memory, transmit the indication to another device (e.g., onboard the aircraft or separate from the aircraft, such as a ground control station or maintenance station), or both store and transmit the indication.

In some examples, the exposure events detected based on an output generated by an electrical conductivity sensor may be used for prognostic monitoring of the condition of the aircraft component. In addition, in some examples, the tracking of the exposure events may be used to predict the useful life of the aircraft component for which the sensor is configured to detect the oxidation catalyst exposures. For example, a processor of a system may predict, using a kinetic model, the useful life (e.g., the estimated time until repair or replacement of the component is desirable) of the aircraft component based on the number exposure events alone, or in combination with other factors (e.g., the number of braking events in the case of an aircraft brake assembly component). The relevant number of exposure events can be, for example, the total number of exposure events over a lifetime of the aircraft component, the number of exposure events within a particular time frame, selected by the processor, or the average number of exposure events per unit of time (e.g., per day, week or month). As an example, a processor may debit the life of the aircraft component for each oxidation catalyst exposure event associated with the aircraft component.

In examples in which the aircraft component is a component of an aircraft brake assembly, the number of exposure events determined based on the output of electrical conductivity sensor may be used to determine the cost value for a braking event of the aircraft. The braking event may include any time during which brakes of the aircraft are in use, such as during touchdown, taxiing, parking, emergency usage (e.g., a rejected takeoff), and the like. For example, the number of exposure events may be used to represent braking conditions in the devices, systems, and techniques described by U.S. patent application Ser. No. 14/030,805 by Esposito et al., which is entitled "GENERATION OF COST-PER-BRAKING EVENT VALUES" and was filed on Sep. 18, 2013. U.S. patent application Ser. No. 14/030,805 by Esposito et al. is incorporated herein by reference in its entirety.

As described in U.S. patent application Ser. No. 14/030,805 by Esposito et al., a processor may take into account data representative of conditions during a braking event of an aircraft to determine the cost value associated with the particular braking event, where the cost value may represent the cost of the usage of the brakes during the particular braking event. The cost value determined in this manner may facilitate real-time billing and cost analysis that is more directly correlated to expected wear on the wheel-and-brake assembly during a respective braking event and maintenance following the braking event, in comparison to examples in which a flat cost-per-braking event value is predetermined and applied to all braking events of the aircraft or customer.

FIG. 1 is a conceptual diagram illustrating an example assembly that may include one or more electrical conductivity sensors configured to detect the exposure of an aircraft component to an electrically conductive deicing solution. In the example shown in FIG. 1, the aircraft component is a component of aircraft brake assembly 10, which includes wheel 12, actuator assembly 14, brake stack 16, and axle 18. Electrical conductivity sensor 50 is mechanically connected to a component of assembly 10, and, in particular, actuator housing 30 of actuator assembly 14. Actuator housing 30 may also be referred to as a piston housing in some examples. An oxidation catalyst detection system may include sensor 50 and a processor configured to receive a signal generated by sensor 50 that varies as a function of the electrical conductivity of a substance to which sensor 50 is exposed, and determine, based on the signal, whether assembly 10 was exposed to an electrically conductive oxidation catalyst. Sensor 50 may be positioned on actuator housing 30 so that the fluids and other substances to which actuator housing 30 is exposed is detected by sensor 50.

FIG. 1 illustrates an example brake assembly 10. In other examples, the oxidation catalyst detection system described herein may be used with other brake assemblies having other configurations. In the example shown in FIG. 1, wheel 12 includes wheel hub 20, wheel outrigger flange 22, lug bolt 26, and lug nut 28. Actuator assembly 14 comprises actuator housing 30, actuator housing bolt 32, and a plurality of pistons (not labeled). Brake disc stack 16 includes alternating rotor discs 36 and stators 38, which move relative to each other. Rotor discs 36 are mounted to wheel 12, and in particular wheel hub 20, by beam keys 40. Stator discs are mounted to axle 18, and in particular torque tube 42, by splines 44. Assembly 10 may support any variety of private, commercial, or military aircraft.

Assembly 10 includes wheel 12, which in the example of FIG. 1 is defined by a wheel hub 20 and a wheel outrigger flange 22. Wheel outrigger flange 22 is mechanically affixed to wheel hub 20 by lug bolts 26 and lug nuts 28. During assembly, an inflatable tire (not shown) may be placed over wheel hub 20 and secured on an opposite side by wheel outrigger flange 22. Thereafter, lug nuts 28 can be tightened on lug bolts 26, and the inflatable tire can be inflated.

Assembly 10 may be mounted to an aircraft via torque tube 42 and axle 18. In the example of FIG. 1, torque tube 42 is affixed to axle 18 by a plurality of bolts 46. Torque tube 42 supports actuator assembly 14 and stators 38. Axle 18 may be mounted on a stmt of a landing gear (not shown) to connect the assembly 10 to an aircraft. During operation of the aircraft, braking may be necessary from time to time, such as during landing and taxiing. Accordingly, aircraft brake assembly 10 may support braking through actuator assembly 14 and brake stack 16. During operation, pistons of actuator assembly 14 may extend away from actuator housing 30 to axially compress brake stack 16 against compression point 48 to provide braking.

Brake stack 16 includes alternating rotor discs 36 and stator discs 38. Rotor discs 36 are mounted to wheel hub 20 for common rotation by beam keys 40. Stator discs 38 are mounted to torque tube 42 for common rotation by splines 44. In the example of FIG. 1, brake stack 16 includes four rotors 36 and five stators 38. However, a different number of rotors and/or stators may be included in brake stack 16. Further, the relative positions of the rotors and stators may be reverse, e.g., such that rotor discs 36 are mounted to torque tube 42 and stator discs 38 are mounted to wheel hub 20.

Rotor discs 36 and stator discs 38 may be mounted in assembly 10 by beam keys 40 and splines 44, respectively. Beam keys 40 may be circumferentially spaced about an inner portion of wheel hub 20. Beam keys 40 may be shaped with opposing ends (e.g., opposite sides of a rectangular) and may have one end mechanically affixed to an inner portion of wheel hub 20 and an opposite end mechanically affixed to an outer portion of wheel hub 20. Beam keys 40 may be integrally formed with wheel hub 20 or may be separate from and mechanically affixed to wheel hub 20, e.g., to provide a thermal barrier between rotor discs 36 and wheel hub 20.

Splines 44 may be circumferentially spaced about an outer portion of torque tube 42. Splines 44 may be integrally formed with torque tube 42 or may be separate from and mechanically affixed to torque tube 42. In some examples, splines 44 may define lateral grooves in torque tube 42. As such, stator discs 38 may include a plurality of radially inwardly disposed notches configured to be inserted into a spline.

In the example shown in FIG. 1, electrical conductivity sensor 50 is mechanically connected to the actuator housing 30 using any suitable technique. For example, sensor 50 may be connected to housing 30 with the aid of a mechanical attachment mechanism (e.g., a bolt, screws, or clamps), or may be adhered to housing 30, welded to housing 30, or any combination of the aforementioned techniques or other techniques. Electrical conductivity sensor 50 is positioned relative to assembly 10 to detect the exposure of assembly 10 to an electrically conductive oxidation catalyst, such as a deicing fluid. In some examples, as described in further detail with respect to FIGS. 5A and 5B, sensor 50 may include a detection portion; when a substance is applied to the detection portion, sensor 50 generates a signal indicative of the conductivity of the electrical path including the substance. Thus, if an electrically conductive fluid accumulates on the detection portion, sensor 50 may generate a signal indicative of a relatively high conductivity, which may indicate the presence of the electrically conductive fluid. Sensor 50 may be connected to housing 30 such that the detection portion of sensor 50 faces in a direction that will increase the likelihood of exposure of the detection portion to the fluids on a runway or other surface when the aircraft is on the ground. For example, sensor 50 may be connected to housing 30 such that the detection portion faces away from brake disc stack 16.

In some cases, an electrically conductive oxidation catalyst may cause premature aging of rotor discs 36 and stator discs 38, which may be formed from a carbon-carbon composite. Thus, in some examples, such as the one shown in FIG. 1, electrical conductivity sensor 50 may be positioned in a location on the brake assembly 10 that will allow the detection portion of sensor 50 to be exposed to substances (e.g., from a runway) to which rotor discs 36 and stator discs 38 may also be exposed. In this way, a signal generated by electrical conductivity sensor 50 indicative of the conductivity of a substance to which sensor 50 is exposed may be used to detect the exposure of rotor discs 36 and stator discs 38 to the electrically conductive oxidation catalyst.

In some examples, sensor 50 is also positioned in a location that does not experience significant motion, such as spinning parts, or rises in temperature. Actuator housing 30 is an example of such a location. The motion may reduce the amount of fluid (or other substance) that may accumulate on the detection portion of sensor 50 during a ground operation of the aircraft, and, therefore, may affect the ability of sensor 50 to generate a signal indicative of the presence of an electrically conductive substance. In other example, instead of actuator housing 30, electrical conductivity sensor 50 may be mechanically connected to another portion of assembly 10, such as, but not limited to, torque tube 42, wheel 12, or axle 18, or to another portion of the aircraft, such as a wheel well, landing gear (shown in FIG. 3), or a portion of the aircraft fuselage or wing.

Although FIG. 1 illustrates a single electrical conductivity sensor, in other examples, an oxidation catalyst detection system may include multiple electrical conductivity sensors configured to detect the presence of an electrically conductive deicing solution or another electrically conductive oxidation catalyst. The electrically conductive sensors may be positioned on the same aircraft component, or may be distributed around an aircraft at a plurality of different aircraft components.

Figure 2:
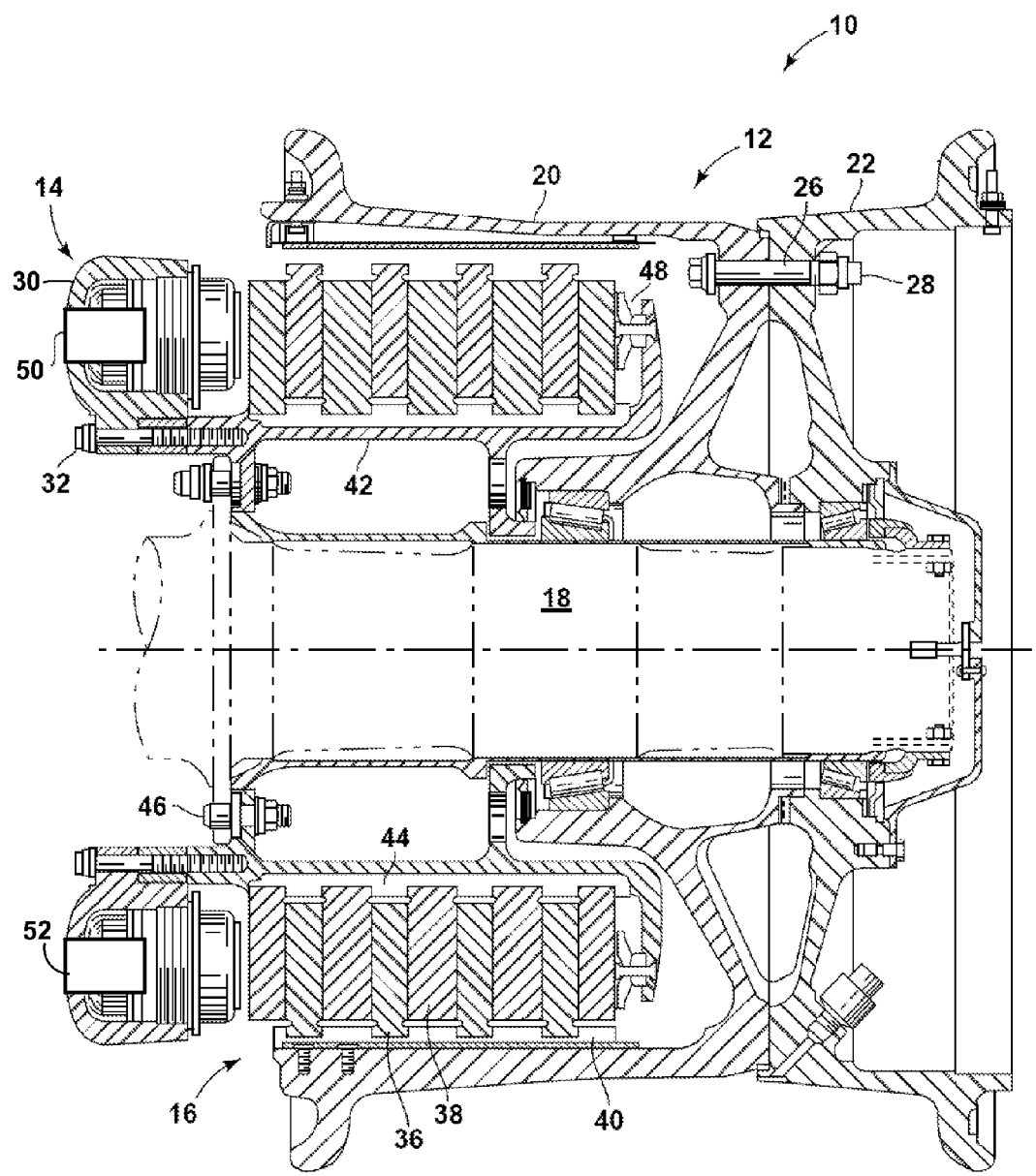
FIG. 2 is a schematic diagram illustrating an example aircraft brake assembly and an array of electrical conductivity sensors mechanically connected to the aircraft brake assembly.

FIG. 2 is a conceptual diagram illustrating an example assembly that includes an array of electrical conductivity sensors. In particular, FIG. 2 illustrates an aircraft brake assembly 10, which includes an array of sensors comprising at least a first electrical conductivity sensor 50 and a second conductivity sensor 52 mechanically connected to the actuator housing 30 on either side of an axle 18. Each sensor in the array can be configured to generate a signal indicative of the presence of an electrically conductive oxidation catalyst. In other examples, sensors in the array can be located at a variety of locations in the assembly (FIG. 1) or in the greater aircraft structure, including the torque tube 42, wheel well (not shown in FIG. 2), landing gear (shown in FIG. 3), and aircraft fuselage or wing (not shown in FIG. 2). An array of electrical conductivity sensors, each positioned at a different location, will increase the possibility that an oxidation catalyst detection system (of which the array of electrical conductivity sensors is part) will detect the presence of an electrically conductive oxidation catalyst and detecting an exposure event. Furthermore, in examples in which the sensors of the array of electrical conductivity sensors are located on at least two different aircraft components, the array of sensors may allow the system to monitor the catalyst exposure of a plurality of aircraft components.

Although only one sensor 50, 52 is shown at a particular location on housing 30 in the example shown in FIG. 2, in some examples, multiple sensors may be connected to actuator housing 30 (or another component) adjacent to each other in order to increase the surface area sensed by the electrical conductivity sensors. This may help increase the probability that an oxidation catalyst detection system disclosed herein may detect the exposure of assembly 10 to the catalyst. The sensors attached to a common component can be arranged in a regular array (e.g., a uniform grid of sensors) or a nonuniform array (e.g., a grid in which the sensors are spaced inconsistent distances from each other).

As shown in FIG. 1 and FIG. 2, in some examples, a single electrical conductivity sensor or a plurality of electrical conductivity sensors can be mechanically connected to a component of aircraft brake assembly 10. In another example, the electrical conductivity sensors of the system may also be positioned on another aircraft component, such as the landing gear of the aircraft, and/or may be distributed around an aircraft at a plurality of different aircraft components.

Figure 3:
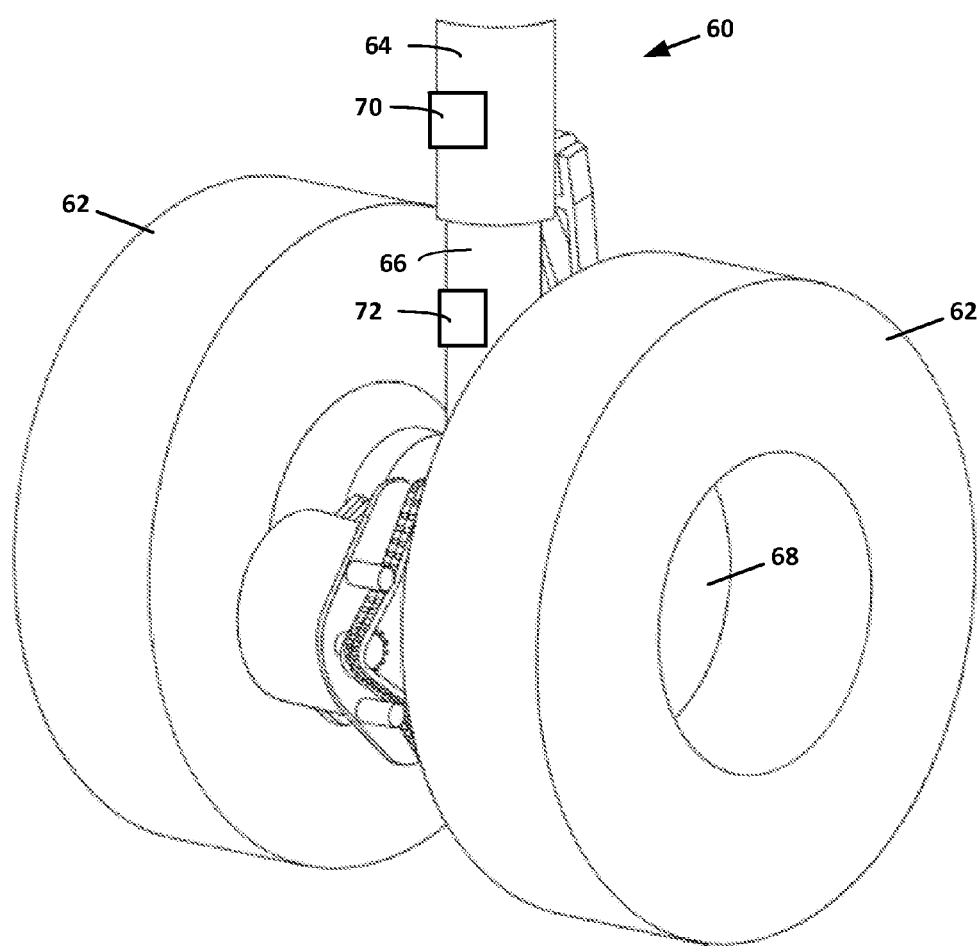
FIG. 3 is a conceptual perspective view of an example aircraft landing gear assembly and an electrical conductivity sensor mechanically connected to the aircraft landing gear assembly.

FIG. 3 is a perspective diagram illustrating an example aircraft landing gear assembly 60, to which electrical conductivity sensors 70, 72 are mechanically connected. An aircraft may be equipped with one or more landing gear assemblies 60. In the example shown in FIG. 3, landing gear assembly 60 comprises aircraft tires 62, cylinder 64, piston 66, and hub 68. During a landing operation or a ground operation (e.g., taxiing), components of assembly 60 may be exposed to a deicing fluid or another oxidation catalyst on the ground. Thus, it may be desirable to position sensors 70, 72 to detect the exposure of assembly 60 (or a particular portion of assembly 60) to the oxidation catalyst in order to better predict the life of assembly 60.

Sensors 70, 72 may be mechanically connected to any suitable portion of landing gear assembly 60 in order to detect exposure of a portion of assembly 60 to an electrically conductive oxidation catalyst. Sensors 70, 72 may be mechanically connected to a component of landing gear 60 that does not experience significant motion or increases in temperature. For example, in the example shown in FIG. 3, electrical conductivity sensor 70 is mechanically connected to cylinder 64 and electrical conductivity sensor 72 is mechanically connected to piston 66.

Although landing gear assembly 60 having a particular configuration is shown in FIG. 3, in other examples, a landing gear assembly to which one or more electrical conductivity sensors of an oxidation catalyst detection system are attached may have any suitable configuration.

Figure 4:
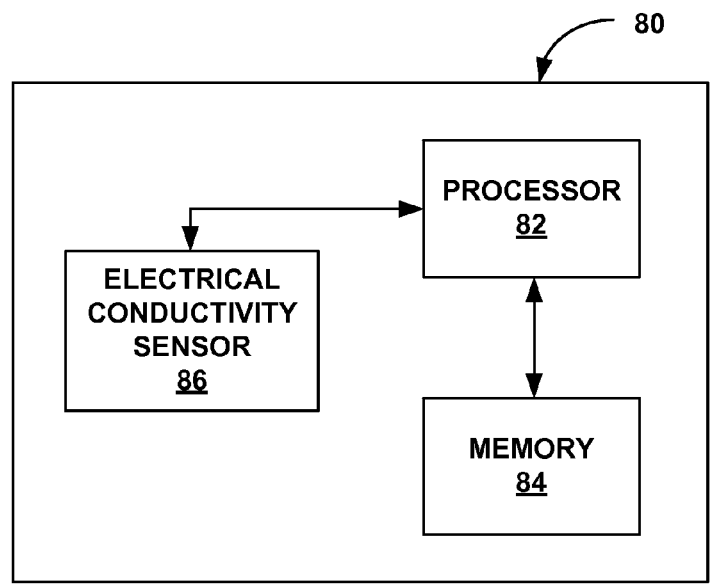
FIG. 4 is a block diagram illustrating an example oxidation catalyst detection system.

FIG. 4 is a schematic functional block diagram illustrating an example oxidation catalyst detection system 80 configured to detect the exposure of an aircraft component to an electrically conductive oxidation catalyst. In the example shown in FIG. 4, system 80 includes processor 82, memory 84, and electrical conductivity sensor 86. Sensor 86 is mechanically connected to an aircraft component, such as a component of aircraft brake assembly 10 (FIG. 1), a component of landing gear 60, or another component of an aircraft. For example, sensor 86 may be sensor 50 shown in FIG. 1, one or both sensors 50, 52 shown in FIG. 2, one or both sensors 70, 72 shown in FIG. 3, or any other electrical conductivity sensor mechanically connected to a plurality of aircraft components. Processor 82 and memory 84 may be located onboard an aircraft in some examples, e.g., in the fuselage of the aircraft or another suitable location.

Electrical conductivity sensor 86 can be any suitable electrical conductivity sensor configured to generate a signal indicative of the electrical conductivity (also referred to as specific conductance) of a substance to which a detection portion (e.g., a detection surface) of sensor 86 is exposed. For example, sensor 86 may include electrodes (e.g., defined by concentric rings) a fixed distance from each other and a conductivity meter configured to generate an output indicative of the resistance of a substance in contact with the electrodes. An example of a suitable electrical conductivity sensor 86 is described with respect to FIGS. 5A and 5B. In some examples, the electrical signal changes as a function of the impedance of an electrical path including the substance (thereby changing as a function of the conductivity of the substance) or as a function of the conductivity of the substance itself. The substance may be passively placed on the detection portion of sensor 86 during operation of the aircraft. For example, if sensor 86 is mechanically connected to aircraft brake assembly 10, the substance may be fluids from the runway that are sprayed towards sensor 86 by the tires of the aircraft wheel assembly with which brake assembly 10 is associated.

Electrical conductivity sensor 86 may be configured to generate an electrical signal indicative of the electrical conductivity of the substance on the detection portion of sensor 86 using any suitable technique. For example, as described with respect to FIGS. 5A and 5B, the substance on the detection portion may form part of an electrical path, and sensor 86 may include a conductivity meter configured to generate a signal indicative of the impedance of the electrical path. The impedance of the electrical path may change as a function of the conductivity of the substance. In this example, processor 82 may determine the electrical conductivity of the substance based on the impedance indicated by the signal generated by sensor 86. The signal may indicate any suitable value indicative of electrical impedance, such as a resistance value, a reactance value, a complex impedance value that includes a resistance component and a reactance component, or the like. In other examples, processor 82 may use other electrical parameter values to determine the electrical conductivity of the substance on the detection portion of sensor 86.

Processor 82 is configured to receive the electrical signal generated by sensor 86 and determine, based on the signal, the electrical conductivity of any substances to which the sensor 86 is exposed. For example, processor 82 may be wired to sensor 86 or may be communicatively coupled to sensor 86 via a wireless communication link. Memory 84 may store one or more electrical conductivity values (e.g., a range of conductivity values) indicative of an electrically conductive oxidation catalyst. Processor 82 may compare the electrical conductivity determined based on the signal generated by sensor 86 to the stored electrical conductivity values and, in response to determining the determined electrical conductivity substantially matches (e.g., matches or nearly matches) the stored electrical conductivity values (e.g., falls within the stored range of conductivity values), processor 82 may determine that the aircraft component to which sensor 86 is mechanically connected was exposed to an electrically conductive oxidation catalyst. The determined and stored electrical conductivity values can also refer to impedance value in some examples.

In some examples, in response to determining the aircraft component to which sensor 86 is mechanically connected was exposed to an electrically conductive oxidation catalyst, processor 82 may generate an indication of an oxidation catalyst exposure event, and store the indication in memory 84. The indication can be, for example, a flag, value, or other parameter stored by memory 84 and associated with an oxidation catalyst exposure event. If system 80 includes multiple electrical conductivity sensors 86, at least two of the electrical conductivity sensors being on different aircraft components, processor 82 may associate the oxidation catalyst exposure event with the aircraft component to which the sensor 86 that generated the output indicative of the presence of the oxidation catalyst is connected. For example, processor 82 may associate the oxidation catalyst exposure event with aircraft brake assembly 10 shown in FIG. 2 if either sensor 50 or sensor 52 generated the electrical signal indicative of the presence of the electrically conductive oxidation catalyst.

Processor 82 may, in some examples, transmit (e.g., via a datalink) the indications of the oxidation catalyst exposure events to another device external to the aircraft, such as a central device used to monitor the useful life of aircraft components for a particular airline. For example, processor 82 may transmit information about the oxidation catalyst exposure events (e.g., the number of events, the date and time of events, the aircraft component(s) with which the events are associated, and the like) to a ground station via an Aircraft Communications Addressing and Reporting system (ACARS). Thus, in some examples, system 80 includes a communications module with which processor 82 may transmit the information about the oxidation catalyst exposure events to another device. In other examples, processor 82 may use another communications module with which the aircraft is already equipped.

In some examples, processor 82, or another processor (e.g., a processor at a ground station) may predict the life of a particular aircraft component based on the stored indications of the oxidation catalyst exposure events associated with the aircraft component. For example, processor 82 may predict, using a kinetic model, the life the aircraft component based on the number exposure events alone, or in combination with other factors (e.g., the number of braking events in the case of an aircraft brake assembly component). As discussed above, the relevant number of exposure events can be, for example, the total number of exposure events over a lifetime of the aircraft component, the number of exposure events within a particular time frame, selected by the processor, or the average number of exposure events per unit of time. In addition, in some examples in which the aircraft component is a component of aircraft brake assembly 10, processor 82 (or another processor) may determine the cost value for a braking even of the aircraft based on the number of exposure events, e.g., using the devices, systems, and techniques described by U.S. patent application Ser. No. 14/030,805 by Esposito et al.

Processor 82 may include any one or more of a microprocessor, a controller, a digital signal processor (DSP), an application specific integrated circuit (ASIC), a field-programmable gate array (FPGA), or equivalent discrete or integrated logic circuitry. The functions attributed to processor 82 in this disclosure may be embodied as software, firmware, hardware and combinations thereof. Processor 82 is also communicatively connected to memory 84, which may include any volatile or non-volatile media, such as a random access memory (RAM), read only memory (ROM), non-volatile RAM (NVRAM), electrically erasable programmable ROM (EEPROM), flash memory, and the like. In some examples, memory 84 may store information about oxidation catalyst exposure events, such as the time and date at which the exposure event was detected, as well as the aircraft component associated with the event. Memory 84 may additionally store instructions for execution by the processor 82 that cause processor 82 to exhibit the functions described herein.

Although not shown in FIG. 4, in some examples, processor 82 may include one or more noise conditioning/filtration components to help filter the signal generated by sensor 86.

Figures 5A, 5B:
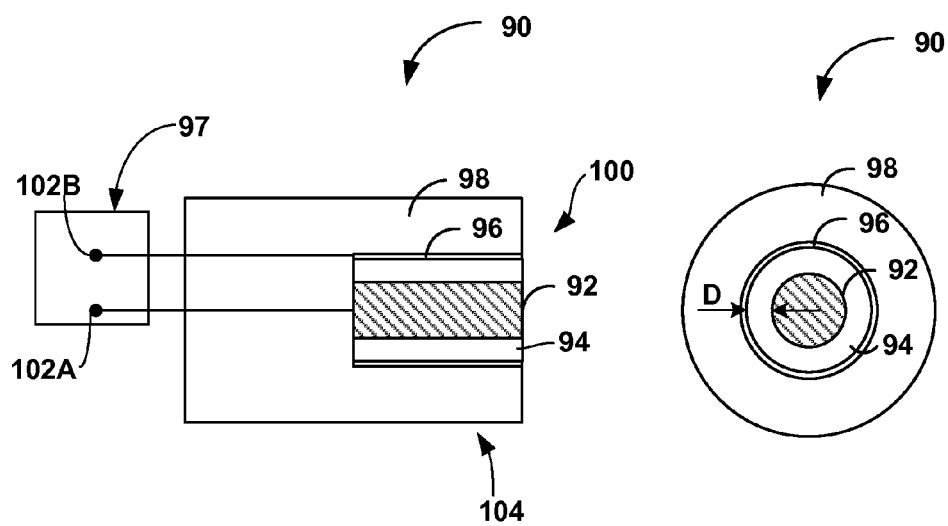
FIGS. 5A and 5B are conceptual illustrations of an example coaxial electrical conductivity oxidation catalyst detection sensor.

FIGS. 5A and 5B illustrate an example electrical conductivity sensor 90, which may be an example of electrical conductivity sensors 50, 52, 70, 72, or 86. In this example, as shown in FIG. 5A, electrical conductivity sensor 90 comprises conductivity meter 97, and conductivity cell 104 including central wire 92, insulator tube 94, surrounding sleeve 96, and surrounding material 98. FIG. 5B illustrates a side view of sensor 90 and illustrates central wire 92, insulator tube 94, surrounding sleeve 96, and surrounding material 98. Electrical conductivity sensor 90 may be configured to generate an electrical signal indicative of an impedance of a solution (also referred to herein as a "substance"), such as deicing fluid, on a detection portion 100 of sensor 90. A side view of detection portion 100 is shown in FIG. 5B. As shown in FIG. 5B, central wire 92 and surrounding sleeve 96 define concentric rings. In some examples, the detection portion of sensor 90 (the surface shown in FIG. 5B) may be polished (e.g., via an electrochemical process) such that central wire 92 and surrounding sleeve 96 are perpendicular to the face.

Central wire 92 and surrounding sleeve 96 act as electrodes of sensor 90 and are a fixed distance D from each other. Wire 92 and sleeve 96 may be formed from any suitable electrically conductive material, such as a relatively low corrosion material suitable for withstanding a highly ionic environment caused by the periodic exposure to the oxidation catalysts. For example, central wire 92 may be a titanium wire that has been coated with platinum and has a diameter of at least about 1 millimeters (mm) in some examples. In addition, in some examples, surrounding sleeve 96 may be a titanium sleeve that has been coated with platinum, and may have a diameter of at least 2 mm. Insulator tube 94 surrounds central wire 92 and sleeve 96, and electrically isolates wire 92 and sleeve 96. Insulator tube 94 may be formed from any suitable dielectric material, such as Tetrafluoroethylene (TFE).

The materials with which insulator tube 94, as well as other components of sensor 90, are formed are selected to be capable of handling the expected operating temperatures of the aircraft component to which sensor 90 is attached. The operating temperatures depend on the location of the sensor on the aircraft. For example, in examples in which sensor 90 is mounted on aircraft brake assembly 10 (FIG. 1), insulator tube 94 is formed from a material capable of handling the brake assembly operating temperatures, which may also vary based on the specific location of assembly 10 sensor 90 is mounted.

Central wire 92, insulator tube 94, and surrounding sleeve 96 are potted in a surrounding material 98, which may comprise a solid or gelatinous compound. For example, surrounding material 98 may be an epoxy in some examples. Surrounding material 98 may provide sensor 90 with improved resistance to shock and vibration, compared to examples in which a surrounding material 98 is not used. For example, surrounding material 98 may help central wire 92, insulator tube 94, and surrounding sleeve 96 maintain their relative positions, even in the presence of shocks or vibrations.

Central wire 92 and sleeve 96 act as electrodes of conductivity sensor 90. Thus, wire 92 and sleeve 96 are also referred to herein as electrodes 92, 96. Electrodes 92, 96 may, but need not, have the same surface area along detection portion 100. Conductivity bridge 97 is electrically connected to electrodes 92, 96 via lead wires 102A, 102B, respectively. For example, wire 102A may be electrically connected to electrode 92 via a solder connection and wire 102B may be electrically connected to electrode 96 via a solder connection. Processor 82 may apply a suitable cell constant to calibrate the output from conductivity bridge 97, e.g., as compared to a standard conductivity cell having two plates, each having a surface area (along detection portion 100) of at least 1 square centimeter ($cm^2$) and being spaced about one centimeter from each other. The dimensions of conductivity cell 104, as well as other dimensions of sensor 86 or other features described herein may be different in other examples.

A substance (e.g., a drop of deicing fluid) may be incidentally be deposited on detection portion 100 during operation of the aircraft (e.g., as a result of splatter from tires of the aircraft or another vehicles), such that the substance is in contact with both electrodes 92, 96. The size of sensor 90 may be selected such that a relatively low volume of substance, such as a droplet having a diameter of about 0.3 millimeters or greater (a volume of 0.0071 $mm^3$ assuming a hemispherical drop) in some examples, is required to bridge the gap between the inner diameter of electrode 96 and the outer diameter of electrode 92 (shown as distance D between the concentric rings defined by wire 92 and sleeve 96) and close the circuit defined by wire 92, sleeve 96, and wires 102A, 102B. The volume required to bridge the gap between electrodes 92, 96, however, may vary in other examples based on the dimensions of sensor 90. The electrical impedance of the circuit is indicative of the electrical conductivity of the substance.

In some examples, in order to determine the electrical conductivity of the substance, processor 82 (FIG. 3) may determine the electrical impedance of the electrical path including wires 102A, 102B, wire 92, the substance that extends across the gap D, and sleeve 96. For example, conductivity meter 97 may be a high impedance ohmmeter (not shown in FIG. 4) or another conductivity meter, such as a voltmeter, that generates an output indicative of the impedance. As another example, conductivity meter 97 may be a Wheatstone bridge circuit, a potentiometer, or another suitable electrical conductivity bridge. The conductivity bridge circuit may generate an electrical signal that indicates the electrical impedance of the electrical path including wires 102A, 102B, wire 92, the substance that extends across the gap D, and sleeve 96.

Processor 82 may apply any suitable cell constant to determine the electrical impedance of the electrical path defined by wire 92, the substance that extends across the gap D, sleeve 96, and wires 102A, 102B. The cell constant may depend on the dimensions of conductivity cell 104 (e.g., the surface areas of electrodes 92, 96 and/or the distance D between electrodes 92, 96).

Although not shown in FIG. 4, system 80 may include a power (e.g., current or voltage) source that, under the control of processor 82, may introduce a current or voltage across wire 92 and sleeve 96 via wires 102A, 102B. In some examples, the input to sensor 90 from the power source may be an alternating current. In some examples, electrical conductivity sensor 90 may also be further connected to other circuitry (e.g., a nulling circuit) to minimize current flow across the electrodes (e.g., wire 92 and sleeve 96) to reduce polarization and corrosion.

Sensor 90 is an example of an electrical conductivity sensor that is not ion specific, but, rather, generates an output that changes as a function of the total ions in the substance. Other electrically conductive sensors that may be used with system 80 or other systems described herein may include, for example, other non-ion specific electrical conductivity sensors, a sensor including ion sensitive electrodes that are sensitive to particular metals known to be in the substance of interest (e.g., deicing fluid), or a solid state electrode that is tuned to detect the presence of specific metals in the substance of interest.

Figure 6:
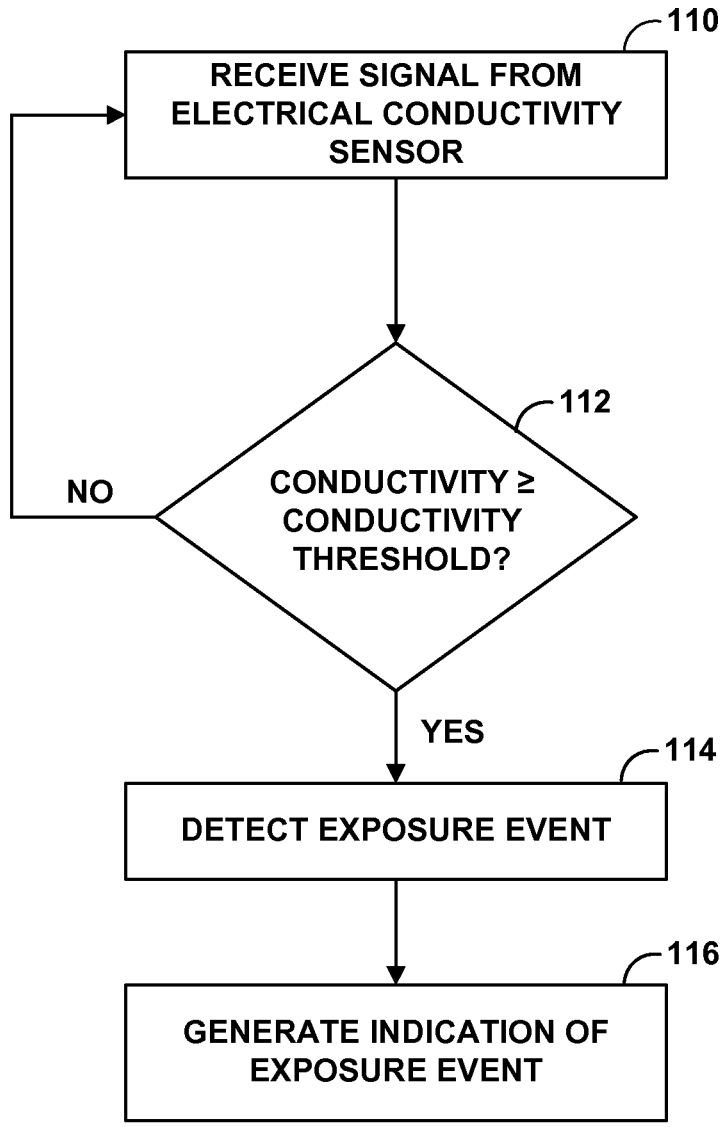
FIG. 6 is a flow diagram illustrating an example method of detecting an oxidation catalyst exposure event.

FIG. 6 is a flow diagram that illustrates an example technique for detecting an oxidation catalyst exposure event. While the technique is described with respect to processor 82 of system 80, in other examples, part or all of the technique may be implemented by another processor, alone or in combination with processor 82. For example, one or more electrical conductivity sensors mechanically connected to aircraft components may be electrically connected to a processor of a device used for another purposes on the aircraft, such as a flight management or communication system.

In accordance with the technique shown in FIG. 6, processor 82 receives an electrical signal from electrical conductivity sensor 86 (110), e.g., via a wired or wireless connection. In some examples, processor 82 controls sensor 86 to generate the signal. For example, processor 82 may cause an input electrical signal to be applied to sensor 86 in order to excite sensor 86. The input electrical signal may have a frequency in the range of 0.1 kilohertz (kHz) to about 5 kHz, such as about 1 kHz, although other signals may also be used in other examples.

Processor 82 compares the electrical conductivity indicated by the signal to a predetermined electrical conductivity threshold value (112), which may be stored by memory 84 of system 80 (FIG. 4). For example, if the signal indicates an impedance, processor 82 may compare the impedance to an impedance value stored by memory 84 and determine the conductivity is greater than or equal to the predetermined conductivity threshold value in response to determining the impedance is less than or equal to the stored impedance value. In some examples, processor 82 applies a cell constant (calibration constant) factor to the received signal prior to comparing it to the predetermined conductivity threshold.

The predetermined conductivity threshold value may be selected (e.g., by a user or by processor 82) to be high enough to help reduce false positive detections of electrically conductive oxidation catalysts. The false positives may arise from, for example, deicer build-up on a detection portion of sensor 86 (e.g., detection portion 100 of sensor 90) that is later exposed to water, or from relatively electrically conductive water (e.g., due to the minerals in the water), or from any other source. In one example, the predetermined conductivity threshold value is 30 mSm/cm.

In response to determining the conductivity is greater than or equal to the predetermined conductivity threshold value, processor 82 detects an electrically conductive oxidation catalyst exposure event (114), and generates an indication of an exposure event (116), which processor 82 may store in memory 84. In response to determining the conductivity is less than the predetermined conductivity threshold value, processor 82 continues to monitor the signal from sensor 86 (110).

In some examples, processor 82 also generates a notification of the detection of the exposure event. For example, processor 82 may generate a visual, audible, or somatosensory alert that a flight crew member of the aircraft receives.

In addition, or instead, processor 82 may generate and transmit the indication to another device, which may be onboard the aircraft or may be external to the aircraft.

Processor 82 may receive an electrical signal from sensor 86 and determine whether the signal is indicative of an electrically conductive oxidation catalyst exposure event, in accordance with the technique shown in FIG. 6, at any suitable frequency. The frequency may be selected to minimize polarization errors. For example, processor 80 may be configured to control the ohmmeter (or other measurement device) of sensor 86 to measure the impedance of the electrical path including the substance on a detection portion of sensor 86 at a frequency of about 1000 Hz.

While the technique shown in FIG. 6 is described with respect to components of system 80 and a single electrical conductivity sensor 86, in other examples, the technique may be applied to system 80 including a plurality of electrical conductivity sensors. For example, processor 82 may be configured to receive the output of a plurality of sensors and determine, for each output, whether the output indicates an electrically conductive oxidation catalyst exposure event.

The techniques of this disclosure may be implemented in a wide variety of computing devices. Any components, modules or units have been described provided to emphasize functional aspects and does not necessarily require realization by different hardware units. The techniques described herein may be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset.

As mentioned above, the techniques of this disclosure may also be implemented on an article of manufacture comprising a computer-readable storage medium. The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the devices described herein may define a specific machine that is capable of executing the specific functions described herein. Also, the techniques could be fully implemented in one or more circuits or logic elements, which could also be considered a processor.

Various examples have been described. These and other examples are within the scope of the following claims.

What is claimed is:

1. A system comprising:
an aircraft brake assembly;
an electrical conductivity sensor mechanically connected to the aircraft brake assembly and configured to generate an output; and
a processor configured to detect an oxidation catalyst exposure event based on the output generated by the electrical conductivity sensor by at least:
determining an electrical conductivity value based on the output of the electrical conductivity sensor,
comparing the electrical conductivity value to a predetermined conductivity threshold value, and
detecting the oxidation catalyst exposure event in response to determining the electrical conductivity value is greater than or equal to the predetermined conductivity threshold value.

2. The system of claim 1, further comprising a memory, wherein the processor is configured to store an indication of the oxidation catalyst exposure event in the memory.

3. The system of claim 1, wherein the threshold conductivity value is 30 millisiemens/centimeter (mS/cm).

4. The system of claim 1, wherein the electrical conductivity sensor comprises a conductivity meter and two electrodes, the conductivity meter being configured to generate the output, the output being a function of an impedance of a substance positioned between the two electrodes.

5. The system of claim 1, wherein the electrical conductivity sensor comprises an array of electrical conductivity sensors mechanically connected to the aircraft brake assembly, and wherein the processor is configured to detect the oxidation catalyst exposure event based on the output of at least one electrical conductivity sensor of the array.

6. The system of claim 1, further comprising a plurality of aircraft components including the aircraft brake assembly, wherein the electrical conductivity sensor comprises a plurality of electrical conductivity sensors, wherein each aircraft component of the plurality of aircraft components is mechanically connected to at least one electrical conductivity sensor of the plurality of electrical conductivity sensors, and wherein the processor is configured to detect the oxidation catalyst exposure event based on the output generated by at least one of the electrical conductivity sensors.

7. The system of claim 1, wherein the aircraft brake assembly includes a piston housing, and wherein the electrical conductivity sensor is mechanically connected to the piston housing.

8. The system of claim 1, wherein the electrical conductivity sensor is a first electrical conductivity sensor, and wherein the output of the first electrical conductivity sensor is a first output, the system further comprising:
an aircraft component, wherein the aircraft component is a wheel well, a landing gear component, or an aircraft fuselage; and
a second electrical conductivity sensor mechanically connected to the aircraft component and configured to generate a second output,
wherein the processor is configured to detect an oxidation catalyst exposure event based on the first output and the second output.

9. A method comprising:
receiving, by a processor, an output of an electrical conductivity sensor mechanically connected to an aircraft brake assembly;
detecting, by the processor, an oxidation catalyst exposure event based on the output, wherein detecting the oxidation catalyst exposure event based on the output comprises:
determining an electrical conductivity value based on the output of the electrical conductivity sensor;
comparing the electrical conductivity value to a predetermined conductivity threshold value; and
detecting the oxidation catalyst exposure event in response to determining the electrical conductivity value is greater than or equal to the predetermined conductivity threshold value;
generating, by the processor, an indication of the oxidation exposure event; and storing the indication of the oxidation exposure event in a memory of a device.

10. The method of claim 9, wherein the aircraft brake assembly includes a piston housing, and wherein the electrical conductivity sensor is mechanically connected to the piston housing.

11. The method of claim 9, wherein the predetermined conductivity threshold value is 30 millisiemens/centimeter.

12. The method of claim 9, wherein the electrical conductivity sensor comprises a conductivity meter and two electrodes, the conductivity meter being configured to generate the output, the output being a function of an impedance of a substance positioned between the two electrodes.

13. The method of claim 9, wherein receiving the output of the electrical conductivity sensor comprises receiving outputs from an array of electrical conductivity sensors mechanically connected to the aircraft brake assembly, and wherein detecting the oxidation catalyst exposure event based on the output comprises detecting the oxidation catalyst exposure event based on the output of at least one electrical conductivity sensor of the array.

14. The method of claim 9, wherein receiving the output of the electrical conductivity sensor comprises receiving outputs from a plurality of electrical conductivity sensors, wherein at least two electrical conductivity sensors of the plurality of electrical conductivity sensors are mechanically connected to different aircraft components including the aircraft brake assembly, and wherein detecting the oxidation catalyst exposure event comprises detecting the oxidation catalyst exposure event based on the output generated by at least one electrical conductivity sensor of the plurality of electrical conductivity sensors.

15. The method of claim 9, wherein the electrical conductivity sensor is a first electrical conductivity sensor, and wherein the output of the first electrical conductivity sensor is a first output, the method further comprising:

receiving, by the processor, a second output of a second electrical conductivity sensor mechanically connected to an aircraft component, wherein the aircraft component is at least one of: a carbon aircraft component, a wheel well, a landing gear component, or an aircraft fuselage;

detecting, by the processor, an oxidation catalyst exposure event based on the first output and the second output.

16. A system comprising:

means for sensing electrical conductivity of a substance to which an aircraft brake assembly is exposed; and means for detecting an oxidation catalyst exposure event based on an output of the means for sensing electrical conductivity, wherein the means for detecting the oxidation catalyst exposure event comprises:

means for determining an electrical conductivity value based on the output of the means for sensing electrical conductivity; and means for comparing the electrical conductivity value to a predetermined conductivity threshold value, wherein the means for detecting detects the oxidation catalyst exposure event in response to determining the electrical conductivity value is greater than or equal to the predetermined conductivity threshold value.

17. The system of claim 16, further comprising:

means for generating an indication of the oxidation catalyst exposure event, based on an output of the means for sensing electrical conductivity; and means for storing the indication.

18. The system of claim 16, wherein the aircraft brake assembly includes a piston housing, and wherein the means for sensing electrical conductivity is mechanically connected to the piston housing.

* * * * *